United States Patent [19]

Perlman

[11] Patent Number: 4,801,529

[45] Date of Patent: Jan. 31, 1989

[54] METHODS FOR ISOLATING MUTANT MICROOGANISMS USING MICROCAPSULES COATED WITH INDICATOR MATERIAL

[75] Inventor: Daniel Perlman, Arlington, Mass.

[73] Assignee: Brandeis University, Waltham, Mass.

[21] Appl. No.: 745,881

[22] Filed: Jun. 18, 1985

[51] Int. Cl.$^4$ .................. C12N 11/04; C12Q 1/70; C12Q 1/18; C12Q 1/04

[52] U.S. Cl. .......................... 435/5; 435/32; 435/34; 435/35; 435/182

[58] Field of Search .............. 435/34, 39, 35, 36, 435/174, 178, 182, 188, 241, 808, 262, 5, 30, 32, 33, 40, 243, 261; 427/4

[56] References Cited

U.S. PATENT DOCUMENTS

| | | | |
|---|---|---|---|
| 3,551,295 | 12/1970 | Dyer et al. | 435/34 |
| 3,856,628 | 12/1974 | Suarra | 435/34 |
| 4,255,411 | 3/1981 | Lim et al. | 424/1 |
| 4,278,761 | 7/1981 | Hastings et al. | 435/178 |
| 4,352,883 | 10/1982 | Lim | 435/178 |
| 4,391,909 | 7/1983 | Lim | 435/178 |
| 4,401,755 | 8/1983 | Weaver | 435/34 |
| 4,401,762 | 8/1983 | Tellier et al. | 435/283 |
| 4,407,957 | 10/1983 | Lim | 435/178 |
| 4,409,331 | 10/1983 | Lim | 435/178 |

*Primary Examiner*—Elizabeth C. Weimar
*Attorney, Agent, or Firm*—George W. Neuner; Ronald I. Eisenstein

[57] ABSTRACT

A method is disclosed for isolating a mutant microorganism. The method includes the following steps:

(1) separately microencapsulating individual or small numbers of a microorganism population containing the mutant to obtain a first microdroplet;

(2) thereafter surrounding the first microdroplet, with or without an outer semi-permeable membrane, with an outer gel-coating to obtain a gel-coated microdroplet, wherein the gel layer contains an indicator material which reacts to the presence of the mutant microorganism;

(3) culturing the resultant microcapsules so that the microdroplets containing mutant microorganism are able to induce a detectable difference in the indicator material from microdroplets, containing non-mutant microorganisms; and (4) separating the microdroplets containing mutant microorganisms from those containing non-mutant microorganisms based upon the differences in the indicator material.

30 Claims, No Drawings

METHODS FOR ISOLATING MUTANT MICROOGANISMS USING MICROCAPSULES COATED WITH INDICATOR MATERIAL

FIELD OF THE INVENTION

The present invention relates to a method for isolating mutant microorganisms from a population containing the same by microencapsulation techniques and to coating microcapsules with indicator materials for practicing the methods of this invention.

BACKGROUND OF THE INVENTION

The enormous size of microbial populations continues to be a great asset in a variety of genetic studies including searches for valuable mutant microorganisms where it is possible to effectively select a rare gene type or mutant microorganism. Mutant cell varieties of a single strain of microorganism (procaryotic, eucaryotic or viral) have classically been isolated by a variety of methods including positive cell "selection" and differential "screening" of individual cell colonies.

Selection is used to isolate mutant varieties of microorganisms when a genetic alteration provides the microorganism with a positive growth advantage over its parental population. For example, acquisition of antibiotic resistance can be used to select such mutants on a nutrient agar surface containing the antibiotic. Another example is the acquisition of a biosynthetic gene enabling the organism to grow in a culture medium that would not otherwise support growth.

Mutants which cause only a small change, a negative change (decrease) or no change in the rate of cell growth are identified by screening of cell colonies. The colonies are produced by multiplication of a single cell. Screening is used to detect mutant microorganism species producing beneficial increases (or decreases) in the synthesis (or the breakdown) of important primary and secondary metabolites for example. However, screening to identify a mutant colony can require examination of tens of thousands of individual colonies to determine the presence of mutants. Replica plating is one screening technique. Thereafter, tedious visual comparison of petri dish pairs are required as well as relatively large amounts of selective and/or restrictive materials which serve to differentiate the mutant from its parent. In general, although screening techniques, are highly effective in achieving the desired result, they are labor and material-intensive requiring examination of many individual colonies, usually in petri dishes.

Recently, a technology has emerged which provides for encapsulating biological material such as living tissue, individual cells, viruses, and biological macromolecules within a semi-permeable membrane. The basic approach in this technique involves suspending the biological material to be encapsulated in a physiologically compatible medium containing a water soluble substance that can be made insoluble in water, e.g., a gel, to provide a temporary environment for the biological material. The medium is formed into droplets containing the tissue and gelled by changing any one of a variety of ambient conditions. These temporary capsules are then subjected to a treatment which results in the production of membranes with a desired permeability (including impermeable membranes). One such technique, is exemplified in U.S. Pat. No. 4,352,883 entitled "Encapsulation of Biological Material", the disclosure of which is incorporated herein by reference.

A description of a technique for separating cells having desired properties from a large population is found in U.S. Pat. No. 4,401,755 entitled "Process for Measuring Microbiologically Active Material" which discloses a method for measuring an unknown quantity of microbiologically active material utilizing unencapsulated microdroplet techniques similar to the first stage process of U.S. Pat. No. 4,352,833. The disclosure of U.S. Pat. No. 4,401,755 is also incorporated herein by reference. After preparing a suspension of gel microdroplets, the suspension is processed in an apparatus having the capability of sensing a physical characteristic of individual gel microdroplets to determine the presence or absence of a desired physical characteristic of the biological material in such a droplet.

It is apparent that a need to develop new mutant isolation techniques exists which will reduce the costs and time spent in selection and screening processes used to isolate mutants from their respective parent populations. Microencapsulation technology, as described in the above referenced patents, provides the potential for solving a variety of problems including the labor and cost excesses of prior art mutant microorganism isolation techniques.

SUMMARY OF THE INVENTION

The present invention provides a method for isolating a mutant cell, an otherwise desirable cell, unique cells or cell hybrids (collectively referred to herein as "mutant microorganism") from either its parent population in the laboratory or from a mixed multispecies population such as encountered in agricultural or industrial environments. Single or small numbers of microorganisms from the parent population (containing the mutant which is desired to be isolated) are encapsulated in a semi-permeable membrane by means of microencapsulation techniques. The cells within the microcapsules are cultured, typically dividing and producing substantially pure clones of microorganisms (colonies) within the microcapsules. Either before the growth phase or thereafter, an appropriate diagnostic interactive indicator material, either living or non-living, is microlocalized within a gel layer outside the first microcapsules. The gel layer may optionally, in turn, be encapsulated with an outer semi-permeable membrane to create double microcapsules. Such microcapsules, and the cells within, are then cultured. Using appropriate culturing conditions the microcapsule containing the desired mutant clone will produce a product or products (also termed metabolites) which diffuse outward across the original microcapsule's semi-permeable membrane. When these metabolites encounter the interactive living or non-living indicator material in the external gel coating, physical and/or molecular changes occur which are the basis for detecting and/or isolating the microcapsule containing the mutant microorganism colony. The interactive indicator material may range from unlabelled or labelled molecules, e.g., fluorescent or radioactive antibodies, antigens, enzymes, enzyme substrates, etc. to living cells capable of dividing. In some embodiments simple gel-coated microcapsules are immobilized at the time of assay and the external gel layer converted to a sol. Complexes can thus be assayed in the immediate vicinity of the immobilized microcapsule in a chemically accessible, soluble environment. The microorganism colonies within the microcapsules remain localized and protected for later recovery.

As indicated above, the indicator material is used as the physically or chemically responsive agent for detecting and selecting microcapsules containing mutant microorganisms. A non-inclusive list of characteristics, which can be the basis of identifying and/or separating microencapsulated mutant cells from the microencapsulated parental population, are: increased or decreased indicator cell number, cell mass, cell density or cell size. The amount of an appropriate biochemical indicator substance complexed with a primary or secondary metabolite, diffused outward from a mutant microcapsule, may also be the basis for mutant identification. Based upon such physical and chemical differences among microcapsules, a variety of separation techniques, such as centrifugation, laser-automated microcapsule sorting, microcapsule autoradiography and microcapsule fluorescence screening are available for use.

The present invention overcomes many of the prior art problems associated with isolating mutant microorganisms from parent populations in that, inter alia, it provides in many instances for separation of microcapsules containing the mutants from the microcapsules containing non-mutants without the necessity for classical genetic screening techniques (which involve individual examination of microorganisms) and therefore eliminates the labor and cost excesses of prior art isolation techniques. In other instances, where the parental population also exhibits that characteristic, but to a lesser degree, a particular physical or chemical characteristic, such as the amount of chemical complex formed between indicator material and the diffusible metabolite produced in microcapsules containing mutant cells, is amplified so that the mutant cells within can more easily be separated from a parental population.

DETAILED DESCRIPTION OF THE INVENTION

The present invention, provides a method for isolating a mutant microorganism from a parent microorganism population containing this same mutant. The method utilizes the relatively new technique of microencapsulation of biological material.

The detection and isolation of mutant cells within microcapsules is described in patent application Ser. No. 580,854, filed Feb. 16, 1984, now U.S. Pat. No. 4,649,109 which is incorporated herein by reference. That application discloses the use of detectable physical and chemical differences (e.g., a change in number of microorganisms per microcapsule) between microcapsules containing the desired mutant microorganisms and those containing non-mutant microorganisms to enrich for and to isolate mutant microorganisms from wild type microorganism populations. This detectable difference serves to enable the discrimination, and/or separation and isolation of microcapsules containing the mutant microorganisms. Several methods for discriminating and isolating microcapsules containing mutant cells are described in the above patent application including sedimentation as well as analytical and diagnostic biochemical methods. The latter include methods in which diagnostic reagents are diffused in and out of the microcapsules to detect a difference in the microcapsules containing mutant microorganisms.

The use of the present invention to obtain a mutant producing a desired product is particularly important to the pharmaceutical industry, petrochemical industry and agriculture in obtaining new and/or improved products.

In the present invention, an indicator material, typically cells of an indicator species of microorganism or, alternatively, indicator molecules, are coated on or microencapsulated *around* microcapsules containing the species from which the mutant cells derive. One then isolates microcapsules containing mutant microorganisms based upon the diffusion of unique molecules or altered quantities of molecules from the mutant microorganisms interacting with the diagnostic indicator material situated immediately *outside* the first (or inner) microcapsule. Cumulative differences in the mass of indicator cells, or, in the level of a detectable binding of diffusible metabolite to indicator molecules, are the result of the first microcapsule bearing the mutant cells and thereby provide a basis for identifying and isolating the mutant cells.

The gel-coated or double microcapsular structure allows for the introduction of a species of living cells into the outer gel layer or outer microcapsule for use as an indicator material. The juxtaposition or appropriately chosen cell species allows the detection and isolation of many highly desirable mutant microorganisms from a wild type population. For example, with the introduction of a growth responsive indicator cell species into the outer microcapsule, the presence of mutant cells producing diffusible metabolites can be detected. A mutant may produce increased primary or secondary metabolite levels which cross-feed the indicator cells and thereby stimulate their growth. Alternatively, other mutants may produce increased levels of growth inhibitors which inhibit the division of indicator cells. Still other mutants may increase the proportion of a metabolite being secreted and rendered diffusible and thereby influence the growth rate of appropriately chosen responsive indicator cells. This stimulation or alternatively inhibition of growth of appropriate indicator cells induces a detectable difference (e.g., a change in number of indicator cell microorganism per double microcapsule) between microcapsules containing the desired mutant microorganisms and those containing non-mutant microorganisms. With similarly sized microcapsules, density is highly sensitive to the cell number of a given microorganism population. This detectable difference (such as provided by a difference in indicator cell number) serves to enable the discrimination and/or separation of microcapsules containing mutants from those with non-mutants. Finally, the microcapsules containing mutant microorganisms are isolated from those microcapsules containing non-mutant microorganisms by separation techniques based directly or indirectly on the detectable difference, e.g., a difference in microcapsule density or mass resulting from a change in indicator cell number per microcapsule.

The present invention comprises first, microencapsulating individual microoganisms from a microorganism population which contains the mutant desired to be isolated. Encapsulation of single microorganisms can be accomplished by techniques well-known to those skilled in the art as discussed in detail in U.S. patent application Ser. No. 580,854 now U.S. Pat. No. 4,649,109. In particular, single microorganism encapsulation can be readily achieved by controlling the concentration of the microorganism in suspension so that each microcapsule will receive, on average, one microorganism.

Generally, the microorganism to be encapsulated are prepared in accordance with well-known prior art techniques, as individual (disaggregated) cells are suspended in an aqueous medium suitable for maintaining viability and for supporting the ongoing metabolic processes of the particular microrganism involved. Media suitable for this purpose are available commercially. Similarly, small numbers of microorganisms can be encapsulated in one microcapsule, if so desired.

Microcapsules may be fabricated in virtually any desired diameter with minor diameter fluctuation by appropriate orifice selection. This assures an essentially constant mass among inner microcapsules populated by freely dividing mutant or non-mutant cells.

The microcapsules are formed so that there is a high probability that each microcapsule contains a small number or one unit of microbiologically active material (i.e. microorganism or cell). This can be effected by regulating the dilution of the liquid composition, sol, to be used to produce the microcapsules using knowledge of the size of the microbiologically active material and the predetermined size of the microcapsule to be produced. The regulation of these factors can be determined by conventional Poisson statistical analyses so that the number of microcapsules containing more than the desired number of microbiologically active materials is more than two standard deviations from the mean. It is desirable, for example, to encapsulate zero to one microbiologically active cell per microcapsule in mutant screening and in recombination DNA research (where the object is generally to isolate desirable spontaneous mutant microorganism or genetically engineered microorganisms from a large parental population of such microorganisms).

The preferred encapsulation techinque is that described in the above-referenced U.S. Pat. No. 4,352,883 (Lim). In brief, this approach involves suspending the microorganism to be encapsulated in a physiologically compatible medium containing a water soluble substance that can be made insoluble in water (gelled) to form a temporary protective environment for the microorganisms so encapsulated. The medium is next formed into droplets containing the single microorganism and gelled, for example, by changing ambient conditions such as temperature, pH or the ionic environment. The microdroplets thereby produced may then, preferably, be subjected to a treatment that results in the production of a membrane of a controlled permeability about the shape-retaining temporary capsules.

The microdroplets can be fabricated from any nontoxic, water soluble substance that can be gelled to form a shape-retaining mass by a change of conditions in the medium in which it is placed, and that also comprises plural groups which are readily ionized to form anionic or cationic groups. The presence of such groups in the polymer enables surface layers of the capsule to be cross-linked to produce the desired membrane when exposed to polymers containing multiple functionalities of the opposite charge.

The presently preferred material for forming the microdroplets is a polysaccharide gum, either natural or synthetic, of the type which can be (a) gelled to form a shape-retaining mass by being exposed to a change in conditions such as a pH change or by being exposed to multivalent cations such as $Ca^{++}$; and (b) "cross-linked" or hardened by polymers containing reactive groups such as amine or imine groups which can react with acidic polysaccharide constituents. The presently preferred gum is alkali metal alginate. Other water soluble gums which can be used include guar gum, gum arabic, carrageenan, pectin, tragacanth gum, zanthan gum or acidic fractions thereof. When encapsulating thermally refractory materials, gelatin or agar may be used in place of the gums.

The preferred method of forming the desired semi-permeable membrane about the microdroplets is to "cross-link" surface layers of a gelled gum of the type having free acid groups with polymers containing acid reactive groups such as amine or imine groups. This is typically done in a dilute solution of the selected polymer. Generally, the lower the molecular weight of the polymer, the greater the penetration into the surface of the microdroplet, and the greater the penetration, the less permeable the resulting membrane. Cross-links are produced as a consequence of salt formation between the acid reactive groups of the cross-linking polymer and the acid groups of the polysaccharide gum. Within the limits, semi-permeability can be controlled by selecting the molecular weight of the cross-linking polymer, its concentration, and the duration of reaction. Cross-linking polymers which have been used with success include polyethylenimine and polylysine. Molecular weight can vary, depending on the degree of permeability required, between about 3,000 and 100,000 or more. Good results are obtained using polymers having an average molecular weight on the order of 35,000.

In a preferred embodiment, a semi-permeable membrane is formed around this first microdroplet. This enables single mutant microorganisms to divide within a physical envelope so that whatever physical, chemical and/or biological identity they possess as single mutants (either a constant identity or an inducible property) can be amplified to facilitate the physical separation and recovery of the desired mutant.

Thereafter, these first microcapsules are preferably individually encapsulated in a sol which contains an appropriate diagnostic "indicator material." This indicator material is chosen to interact with primary, secondary, or other metabolites issuing from the mutant microorganisms. The sol consists of the same or similar sol ingredients as contained in the first (inner) microcapsules. The concentration of microcapsules suspended in the sol and the diameter of the sol droplets can be varied to achieve zero to one microcapsule per sol droplet. The sol droplets, which preferably contain zero to one inner microcapsules, are converted to a gel phase by using techniques as described above. The encapsulated first microcapsules may then be incubated under appropriate culturing conditions or alternatively treated with appropriate reagents to form an outer semi-permeable membrane or second microcapsule surrounding the first microcapsules. This results in double membrane microcapsules.

The use of a second, outer semi-permeable membrane has a number of advantages. The sterile environment can be maintained inside the capsule even when there is a non-sterile culture environment outside. Another advantage to using an outer membrane is that the gel may be converted to a sol thereby facilitating chemical diffusion, mixing, cell growth, and assay of molecular complexes in the sol phase. The presence of an outer membrane eliminates the need to physically immobilize individual microcapsules prior to converting the external gel coating to a sol phase for biochemical or immunological assay experiments. The concentric microcapsule structures may be passed through a liquid phase automated cell sorting device to detect fluorescent or otherwise labeled biochemical complexes, etc. within the microcapsules. Alternatively, these labeled microcapsules may be displayed on a two dimensional surface for fluorescence detection, autoradiography, or for other assays.

Choice of the diameters, permeabilities, and chemical composition of the two respective (inner and outer) double microcapsule membrane will depend upon the particular experiment being carried out. The choice of culture media must first permit the growth of cell species from which the mutant is derived. Either simultaneously or subsequently the medium plus the metabolite synthesized and diffused outward by the desired mutant must support growth of the indicator cells. Alternatively, if the mutant is producing a growth inhibitor, such as an antibiotic which reduces the rate of growth of appropriate indicator cells, then the culture medium without this antibiotic should support normal growth of the indicator cells. The growth phase of the indicator cells may be planned to coincide or alternatively follow the growth of the microorganism cell species from which the mutant cells are derived. It is also within the scope of the present invention to include applications in which the microcapsular placement of the mutant cells and the indicator material is reversed. That is, the indicator material could be placed in the inner microcapsule while the cell species containing the mutant is placed in the outer microcapsule.

Isolation of many classes of mutant microorganisms can be achieved by the present double encapsulation process, including spontaneous or induced mutants, cell hybrids formed by uniting cells of different species, and genetically engineered species carrying exogenously introduced genes. The isolation procedure takes advantage of the changes in metabolites and/or their concentrations produced by, and emerging from these mutants. The mutants to be selected synthesize and secrete, or outwardly diffuse, novel, changed, increased or decreased amounts of primary or secondary metabolites. Single or small numbers of cells of one species from which the mutant(s) is derived are cultured to form microcolonies within the microcapsules. These mutants synthesize a wide variety of different metabolites. Although it would be difficult to isolate such a mutant by itself, by choosing the appropriate indicator material, and then selecting for the microcapsule's physical or chemical alteration brought about by that indicator as disclosed herein, the mutant can readily be isolated.

An indicator is chosen that reacts to the presence of the metabolite. In a preferred embodiment, cell species in which the growth rate of the cell is affected by the metabolite are used as indicator material. The choice of a particular indicator species will be determined by the type of mutant one is seeking to isolate, and based upon that goal, the particular species can readily be determined by the skilled practitioner. For example, by choosing as an indicator a cell that has an increase in its rate of growth as a result of exposure to a novel or an increased level of an amino acid, microcapsules containing a mutant producing or overproducing an amino acid can be readily identified. The auxotrophic, amino acid requiring indicator cell species is microencapsulated around the original microcapsules carrying the first cell species. An appropriate culturing period is allowed for growth in a medium which is deficient in the particular amino acid produced by the mutant but otherwise compatible with growth of the indicator cell species. The inner microcapsule membrane is formed so as to permit secretion (or leakage) of the amino acid metabolite from the overproducer mutant cell species. The culture period should allow for a number of generations of indicator cell growth so that the number of indicator cells around mutant microcolonies will be sufficiently different from the number around non-mutant microcolonies to enable detection and/or separation of the mutant microcolonies. The various detection and separation methods are techniques well-known in the art.

For instance, the difference in indicator cell number between microcapsules containing mutant and non-mutant cells permits both simultaneous (bulk or in toto) separation techniques as well as sequential (or serial) separation techniques. Examples of bulk separation include equilibrium density centrifugation, velocity or gravity sedimentation, separation in electrical or magnetic fields, chromatography, etc. Examples of serial techniques include detection of individual microcapsules via radioactive, luminescent, fluorescent or colorimetric labels, etc. Serial detection can be accelerated utilizing automated devices such as laser and automated particle sorting devices.

This present invention can also be used to isolate industrial strains of microorganisms that have been mutated or "improved" to synthesize greater yields of secondary metabolites such as antibiotics. Microencapsulation of single or small numbers of such cells and subsequent re-encapsulation with indicator cells sensitive to the metabolite, e.g., antibiotic, provide a useful system for selecting these improved mutants. The growth rate of the indicator cells reflects the relative amount of antibiotic secreted by the cells under investigation. A selection based on the number of indicator cells in a microcapsule following a growth phase can be performed using mass separation methods, e.g., equilibrium or velocity sedimentation. Alternatively, indicator cell yield per microcapsule may be determined by techniques such as laser automated particle sorting methods which are well known to those familiar with this field.

In another application of this invention, mutants may be selected which synthesize and export novel or increased levels of *macromolecules,* such as proteins, carbohydrates, lipids, and mixed complexes thereof. Protein macromolecules may include enzymes, peptides, hormones, other protein "factors", serum proteins, etc. These mutants are isolated by using indicator cells that exhibit a changed growth rate in response to the exported macromolecule in a manner similar to those examples discussed above. Alternatively, increased production levels of macromolecules may be detected by using indicator materials, rather than living cells, placed in a gel layer around the original microcapsule containing the mutant cells. An indicator material could be an antibody directed against and specifically binding to a desired macromolecule.

This general technique also enables one to select mutants which fail to produce or produce lower amounts of a specific, undesirable or detrimental metabolite. Similarly, mutants producing macromolecules having increased or decreased biological or biochemical specific activities may be produced.

Selection of mutants producing, or overproducing levels of a desired active protein factor, such as an enzyme utilizing a modification of the above basic method, is straightforward. The desired enzyme will convert one or more appropriate precursor substances (described herein as "A") to a product (termed "B"). An indicator cell species is placed in the gel layer surrounding the original microcapsules containing the parent cell population from which the mutant is derived. The indicator species is chosen to respond with a change in growth rate to the increased concentration of B produced by the mutant cells. Substance A, the substrate for the enzyme, may or may not be diffusible through the microcapsule membranes. If it is not diffusible, then it will be co-encapsulated at sufficient concentration, together with the original cells (including the mutant) so that the resultant concentration of product B will be sufficient to cross-feed or alternatively inhibit the indicator cells. If substance A is diffusible, it may be simply added to the microcapsule culture medium. Substance A is converted to product B by the target enzyme. Product B must be diffusible from the inner microcapsule so it can interact with the indicator material. Selection of mutants is based upon detecting the "change" in the indicator material, e.g., a cell mass increase, as a result of its "reaction" with product B. The indirect method of using an external substrate source for revealing elevated enzymes levels in mutant cells contrasts with the direct process described earlier in which their mutant cells are selected by the increased synthesis of primary or secondary metabolites (which directly affect indicator cells). This method can be used to select for mutants producing large amounts of a desired macromolecule.

Target enzymes having commercial importance include the hydrolases which are principally derived from the genera Asperqillus and Bacillus. The extra-cellular secreted hydrolases overproduced by these mutant cells will generally cause increased indicator cell growth rate as a result of cross-feeding of indicator cells with hydrolysis products of proteins (amino acids), polysaccharides (mono- and disaccharide products) and fats (small fatty acids). These hydrolysis products (B) are microcapsule-diffusible. The alteration of indicator cell growth rate and thereby indicator cell mass, permits the detection and separation of microcapsules containing the mutant cells as described above.

In a similar manner, mutant microorganisms may be selected which produce particular enzymes having increased specific activities, increased thermal stabilities, altered substrate specificities or alterations in other intrinsic properties. The microcapsule selection process merely requires that an appropriate indicator material (e.g., living cells) has an opportunity to react, i.e., grow, with product B under culturing conditions which will differentiate between the microcapsules producing the mutant enzyme and microcapsules producing normal enzyme.

This method can be used to isolate a wide variety of mutant microorganisms as shown in the following table: The mutant synthesizes an enzyme which converts substance A to product B. Product B cross-feeds indicator cells which are chosen because they require that nutrient for growth. Alternatively, product B is an inhibitor of cell growth so that increased conversion of substance A to B by mutant microorganism will decrease the indicator cell growth allowing isolation of microcapsules containing mutant microorganisms.

TABLE

| | Enzyme | A | B | Indicator Cells |
|---|---|---|---|---|
| (1) | L-amino acid X aminoacylase | Acylated D, L amino acids (racemic mixture) | L-amino acid X | amino acid X auxotroph |
| (2) | aspartase | ammonium fumarate | L-aspartic acid | aspartate auxotroph |
| (3) | Penicillin acylase type I | penicillin G | 6-aminopenicillanic acid | pencillin sensitive |
| (4) | Pencillin acylase type II | pencillin V | 6-aminopenicillanic acid | pencillin sensitive |
| (5) | Cephalosporin acylase | 7-aminocephalosporanic acid (7-ACA) | cephalothin | cephalosporin sensitive |
| (6) | Cephalosporin acylase | (7-ADCA) | cephalexin | cephalosporin sensitive |
| (7) | Tryptophan synthetase | indole, pyruvate and ammonia | tryptophan | tryptophan auxotroph |
| (8) | Tryptophan synthetase | indole and serine | tryptophan | tryptophan auxotroph |
| (9) | —tyrosinase | phenol, pyruvate ammonia | L-tryosine | tyrosine auxotroph |
| (10) | steroid transformation biosynthetic enzymes | steroid precursor(s) | steriod, e.g., ergosterol | ergosterol requiring yeast mutant |
| (11) | vitamin biosynthetic enzymes | vitamin precursors | vitamins | vitamin-requiring microorganism |

Microorganisms containing exogenous DNA, e.g., vectorially introduced cloned DNA sequences, can also be readily screened. E. coli cells transformed with a mammalian gene for human growth hormone (hGH) are microencapsulated within semi-permeable membranes having porosity sufficient to let the hGH protein through. The microcapsules are reencapsulated in a gel containing mammalian target cells which require the growth hormone for their own growth. The microcapsules are cultured in mammalian growth medium containing a bacteriostatic antibiotic which prevents any free E. coli cells from growing and contaminating the medium. After an appropriate culturing interval, hormone-secreting E. coli cells containing the cloned DNA sequence should contain a greater number of mammalian cells than microcapsules containing E. coli which do not secrete the hGH. The desired microcapsules can be isolated by automated cell-sorting techniques which discriminate microcapsules containing large numbers of mammalian cells from those with only a few mammalian cells. Alternatively, equilibrium or velocity sedimentation can be used to fractionate the microcapsules, based on density difference between microcapsules carrying many versus few cells by techniques well-known to those skilled in the art.

Bacterial mutant strains which accumulate increased amounts of soluble inorganic nutrients (such as phosphate) and convert them to insoluble products (such as polyphosphate) can be easily screened. Such mutants of Acinetobacter and other species are detected by using the reversible nature of this phosphate conversion process coupled with phosphate diffusion cross-feeding. Under aerobic conditions, the cells accumulate insoluble polyphosphate whereas anaerobic cultures hydrolyze this polyphosphate to produce soluble inorganic phosphate. Microcolonies of these cells are first cultured in microcapsules in an aerobic phosphate-rich medium. Subsequently, the microcapsules are re-encapsulated. The outer microcapsules contain a number of low phosphate or phosphate starved cells of any appropriate indicator species (all species require phosphate to grow). The double encapsulated cells are then cultured in an anaerobic, phosphate-free, or very low phosphate, medium which would support growth of the indicator cells, but for the lack of phosphate. Microcapsules containing large amounts of polyphosphate which can be converted to soluble inorganic phosphate to support growth will have greater indicator cell growth. The microcapsules are then assayed and isolated based on indicator cell number. Those possessing the largest number of indicator cells should contain Acinetobacter cells overproducing polyphosphate. This is particularly valuable in obtaining strains that are helpful in agriculture.

Cells secreting new, or increased, levels of catabolic enzymes capable of metabolizing industrial intermediates, synthetics or waste products can also be isolated. The solubility of industrial products such as petrochemicals in aqueous solvent is limited in a number of instances and often the density of these substances is not identical to that of aqueous growth medium. By placing an appropriate amount of such an industrial product in the outer microcapsule and including one or a small number of potential mutant cells within the inner capsule, the metabolism of the product can be followed as the cells grow. The close proximity of the cells to the industrial product favors its metabolism by catabolic enzymes secreted by cells within the same double microcapsule. A poor external growth medium may be desirable to facilitate detection of growth which is enhanced by metabolism of the microencapsulated industrial product. The microcapsules containing mutants metabolizing the industrial product show both an increased cell number and a reduced amount of the original product. These changes e.g., density changes or increased fluorescent cell labelling, are then used to detect and isolate the mutants.

With a similar objective, previously undiscovered or difficult to obtain microorganisms capable of metabolizing, degrading or detoxifying natural or man-made substances, such as organic waste chemicals, petrochemicals, and agricultural by-products, can be isolated from a mixed population of microorganisms. The chemical breakdown of one of these products (termed substance X) by such a microorganism may or may not affect the growth rate of that microorganism. If growth rate is affected, then the microorganism may be isolated by the microencapsulation of single cells followed by growth in the presence of substance X, as described in U.S. patent application Ser. No. 580,854 now U.S. Pat. No. 4,654,109. If not, the microorganism of interest is isolated based upon its ability to metabolize substance X and the use of the present invention. A metabolic breakdown product of substance X provided by the microorganism is used as a nutrient for the growth of another species of microorganism. This second species of microorganism is used as the indicator microorganism. Cells of the original undefined population are grown in appropriate culture medium within microcapsules to form microcolonies. These microcapsules are then re-encapsulated to form double microcapsules each containing indicator microorganisms. These microcapsules are cultured in medium lacking an essential nutrient for growth of the indicator cells. The nutrient will be furnished by the metabolic breakdown of substance X. Indicator cells will selectively grow in those microcapsules which contain an internal microcapsule colony species which is metabolizing substance X (substance X must either be diffusible or be encapsulated originally with the single cells). After a sufficient period of time for growth of the indicator cells, the microcapsules containing larger numbers of indicator cells are separated and the mutant species isolated.

Metabolic interactions between various pairs of microorganisms can also be studied using the present process. By controlling the semi-permeable membrane porosity, an investigator can study cross-feeding of different molecular weight metabolites between the different species.

In the process of forming gel-coated microcapsules, depending upon the volume of sol coating component relative to the inner microcapsule component and upon the final droplet volume, a certain fraction of the gel droplets formed will not include an original microcapsule. These "empty" droplets will not affect mutant microorganism selection because the selection depends upon the interaction of mutant microorganisms with the indicator material. The sol to gel conversion step involving the microcapsule coating is the same process used to form the original microcapsule gel droplets. The present invention includes use of double layered gel microdroplets in mutant isolation where the inner, the outer or both potential semi-permeable membranes surrounding the respective gel layers are absent. Therefore, in one form of the present invention, two gel layers without membranes are present. One layer contains the microorganism species providing mutant cells and the other layer contains the indicator material. This material may include chemical substances, biochemicals, as well as species of living cells different from the mutant as described above. The embodiment where there is no inner semi-permeable membrane is referred to as a gel-coated microdroplet or microencapsulated microdroplet.

When coating the inner microdroplet, care must be used so that the inner microdroplet is not reliquified. This can be done by techniques well known in the art. For example, one can use two different types of gelling, e.g., a calcium gel for the inner microdroplet and a low-melting temperature thermal gel for the outer coating.

However, the use of semi-permeable membranes to regulate diffusion in and out of gel microdroplets and to provide physical barriers for microorganism containment, i.e., sterility, is sometimes essential. These semi-permeable membranes often facilitate microorganism mutant isolation as described above by excluding undesirable substances (e.g., destructive proteases or other cells), by permitting selective passage of desired substances (e.g., diffusion of a metabolite from the mutant cells to indicator cells) and by retaining and thus concentrating desired substances (e.g., use of the outer microcapsule membrane to retain the metabolite from the mutant cells to enhance its effect on indicator substances).

In one embodiment, the outer gel coating is treated with reagents to form an outer semi-permeable membrane as described for the inner microcapsules. The semi-permeable outer membrane, whose porosity and composition may be controlled and may be different from the inner microcapsule membrane, can be used for a number of functions. These functions include: (I) maintaining sterility of the microcapsule in non-sterile culture environments; (II) allowing diffusion of culture medium nutrients to the indicator cells; (III) restricting loss to the culture medium by diffusion of the targeted metabolite produced by the mutant microorganisms (i.e., the metabolite of interest must be diffusible between the inner microcapsule and the outer microcapsule so that it can reach the indicator microorganisms outside the inner microcapsule membrane); and (IV) providing a physical constraint which permits conversion of the gel phase back to the sol phase (for reasons of cell growth, biochemical assays, etc.) without the consequent loss of indicator cells to the surrounding culture medium.

The diameter and thus the volume of the gel coating applied to the microcapsules can be controlled by the ejection orifice diameter and sol viscosity. There is no difficulty with coating the inner microcapsule with an outer gel layer. The microcapsules are sturdy and can readily be ejected after coating. The ratio of outer gel volume to inner microcapsule volume is chosen to suit the experimental application. Thus if the objective of the gel coating is to immobilize macromolecules outside the microcapsule then a thin gel coating will often suffice. If the objective is to allow for cross-feeding and subsequent growth of an indicator species of microorganism within this gel volume then a much thicker coating may be required. If growth of the indicator microorganism (in response to metabolites produced by a mutant colony inside) is to be used for direct physical separation of the mutant-containing microcapsules (e.g., by density sedimentation) then the second capsule must be large enough so that the mass of indicator cells grown in the outer gel layer will alter microcapsule density to allow such a separation as described above. For such a microcapsule density shift to occur, the ratio of gel coating volume to microcapsule volume should range between 0.5:1.0 and 100:1.0. Within this range, the specific ratio is determined by the growth yield (mass) of indicator cells per volume of gel coating (growth density). The growth yield is determined by nutritional factors. In the cross-feeding situations discussed herein, the production level of a desired growth stimulating metabolite from the mutant cells limits this growth yield.

Automated laser sorting may be employed to separate microcapsules containing varying numbers of indicator cells. With chromatic or fluorescent staining of indicator cells the selection method can be sensitive to small overall numbers of indicator cells per microcapsule wherein the indicator cell numbers vary among the microcapsules. That is, in experimental situations which may not generate sufficient indicator cell growth mass to allow density separation of the microcapsules containing the mutant cells, the automated laser sorting method provides a possible alternative separation method. The difference in cell number of the indicator species among the microcapsules still remains the basis for identifying microcapsules containing mutants in the laser method.

The present invention also provides a kit for practicing the methods described above. The kit comprises the ingredients or components required to form microcapsules on a laboratory or research scale to screen for mutants in accord with the present invention. As such, the kit comprises a container or package having quality-controlled reagents therein: sterile alginate solution, sterile 2-(cyclohexylamino)ethane sulfonic acid, indicator material, sterile solution of polylysine having predetermined molecular weight and a sterile solution of polyethylenimine (PEI) having a predetermined molecular weight. The molecular weights of the polylysine and PEI are predetermined to produce microcapsules having a desired permeability in accord with the known technology as described in, for instance, U.S. Pat. No. 4,352,883. In addition, sterile $CaCl_2$ and mechanical devices for forming microdroplets can be supplied as part of the kit. Preferably, the solutions are provided in sealed sterile vials having sufficient quantities for one experiment. Further, it is preferred that the solutions comprise physiological saline and polylysine and PEI solutions also contain 0.2M MOPS.

From the foregoing, it is apparent that isolation of mutant microorganisms in accordance with the present invention, can be practiced on a wide variety of species, using a variety of techniques that result in a difference between indicator material in microcapsules containing mutants and those microcapsules that do not.

It is appreciated that those skilled in the art upon consideration of this disclosure, may make modifications and improvements without departing from the spirit and scope of this invention.

I claim:

1. A method for isolating a mutant microorganism, where the method comprises:
    (a) separately microencapsulating individual or a small number of microorganisms from a microorganism population containing the mutant to obtain a first microdroplet;
    (b) surrounding the first microdroplet, thereby forming an inner microdroplet, with an outer gel-coating to obtain a gel-coated microdroplet, wherein the gel-coating on the microdroplet contains an indicator materials which reacts to the presence of the mutant microorganism;
    (c) incubating the gel-coated microdroplets to induce a detectable difference in the indicator material surrounding microdroplets containing mutant microorganisms; and
    (d) separating the microdroplets containing mutant microorganisms from those containing non-mutant microorganisms based upon the detectable difference in the indicator material.

2. A method for isolating a mutant microorganism, where the method comprises:

(a) separately microencapsulating an indicator material which reacts to the presence of the mutant microorganism to obtain a first microdroplet;

(b) surrounding the microdroplet with an outer gel-coating to obtain a gel-coated microdroplet, wherein the gel-coating contains individual or a small number of microorganisms from a microorganism population containing the mutant;

(c) incubating the gel-coated microdroplets so that the microdroplets containing mutant microorganisms induce a detectable difference in the indicator material; and (d) separating the microdroplets having mutant microorganisms from those having non-mutant microorganisms based upon the detectable difference in the indicator material.

3. The method of claim 1 wherein the indicator material reacts with a metabolite produced by the mutant microorganism.

4. The method of claim 1 wherein the indicator material reacts with a product formed by a reaction between the mutant microorganism and a substance included in its culture medium.

5. The method of claim 1, wherein the inner microdroplets containing the single microorganisms are formed by:

(a) forming a dilute suspension of said microorganisms in a liquid diluent capable of forming a gel upon subsequent treatment, said dilute suspension having a dilution selected so that there is a high probability that each microdroplet produced from said suspension contains one microorganism;

(b) converting said suspension into gel droplets.

6. The method of claim 5, wherein the outer gel coating is formed by:

(a) forming a dilute suspension of indicator material in a liquid diluent capable of forming a gel upon subsequent treatment;

(b) coating the first microdroplet with the suspension from (a);

(c) ejecting the coated microdroplets into a solution which causes the coating to gel, resulting in a gel-coated microcapsule.

7. The method of claim 1, wherein a semi-permeable membrane is formed around the inner microdroplet by cross-linking surface layers of the inner microdroplet resulting in a microcapsule.

8. The method of claim 7, wherein a semi-permeable membrane is formed around the outer gel-coating by cross-linking surface layers of said outer gel-coating resulting in a double membrane microcapsule.

9. The method of claim 7, wherein the indicator material is a species of cells whose growth is affected by a metabolic product of the mutant microorganism.

10. The method of claim 1 wherein before coating the first microdroplet with an outer gel-coating, the microdroplet is cultured for a sufficient time to enable the individual or small number of microorganisms to multiply and form microcolonies.

11. The method of claim 1 where after coating the first microdroplet with an outer gel-coating, the gel-coated microdroplet is cultured for a sufficient time to enable the individual or small number of microorganisms to multiply and form microcolonies.

12. The method of claim 1, wherein said separation is based on the difference in mass of indicator material between said microdroplets containing mutant and non-mutant microorganisms and comprises equilibrium density centrifugation or sedimentation of a suspension containing said microdroplets.

13. The method of claim 9, wherein said separation is based on the difference in mass of indicator material between said microcapsules containing mutant and non-mutant microorganisms and comprises equilibrium density centrifugation or sedimentation of a suspension containing said microdroplets.

14. The method of claim 1, wherein the step of separating the microdroplets containing mutant from non-mutant microorganisms comprises fluorescent, colorimetric, or radioactive sorting of microdroplets in a suspension containing said microdroplets.

15. The method of claim 1, wherein the separation based on the difference in indicator material between said microdroplets containing mutant and non-mutant microorganisms comprises electrical or magnetic sorting of a suspension containing said microdroplets.

16. The method of claim 1, wherein said microorganisms comprise eucaryotic cells.

17. The method of claim 1, wherein said microorganisms comprise procaryotic cells.

18. The method of claim 1, wherein said microorganisms comprise viruses.

19. The method of claim 1, wherein said microorganisms comprise cell hybrids formed by fusing cells of different species.

20. The method of claim 1, wherein mutant microorganisms are incubated in a medium selected from the group consisting of chemically complex, non-sterile, agricultural, industrial, and other commercial process media.

21. The method of claim 9 wherein said growth is effected by amplifying the detectable difference between the indicator species in microcapsules containing the mutant microorganisms and the non-mutant microorganisms, and the separating step is based on physical characteristics amplified thereby.

22. The method of claim 1, wherein the microencapsulated microorganisms are grown in a laboratory culturing medium.

23. The method of claim 7, wherein the inner microencapsulated microorganisms are grown in a non-sterile, multi-species agricultural or industrial process medium wherein one or more species are found in the native environment.

24. The method of claim 1, wherein the mutant microorganism is a naturally occurring mutant of a wild type microorganism.

25. The method of claim 1, wherein the mutation in the mutant microorganism is artificially induced.

26. The method of claim 25, wherein the artificially-induced mutant is the result of genetic engineering by a biological, biochemical or biophysical process.

27. The method of claim 1 wherein the indicator material is a non-living material.

28. The method of claim 27 wherein the non-living indicator material is selected from the group consisting of labelled or unlabelled antibodies, antigens, enzymes, enzyme substrates and combinations thereof.

29. The method of claim 9, wherein said metabolic product of the mutant microorganism is an essential metabolite for said indicator species, and the microcapsules are incubated under conditions restrictive to growth of said indicator species, whereby the microcapsules containing the mutants have a greater number of indicator cells per microcapsule than microcapsules containing non-mutants.

30. The method of claim 9, wherein said metabolic product of the mutant microorganism is an inhibitor of the growth of said indicator species, and the microcapsules are incubated under conditions permissive for growth of said indicator species, whereby the microcapsules containing the mutants have a less number of indicator cells per microcapsules than microcapsules containing non-mutants.

* * * * *